United States Patent [19]

Cantrell

[11] Patent Number: 4,877,611

[45] Date of Patent: Oct. 31, 1989

[54] VACCINE CONTAINING TUMOR ANTIGENS AND ADJUVANTS

[75] Inventor: John L. Cantrell, Corvallis, Mont.

[73] Assignee: Ribi ImmunoChem Research Inc., Hamilton, Mont.

[21] Appl. No.: 102,909

[22] Filed: Sep. 30, 1987

Related U.S. Application Data

[63] Continuation-in-part of Ser. No. 852,120, Apr. 15, 1986, Pat. No. 4,806,352.

[51] Int. Cl.[4] .................... A61K 39/39; A61K 39/04
[52] U.S. Cl. ............................... 424/88; 514/885;
  514/937; 514/938; 514/934; 514/943
[58] Field of Search ................ 424/88, 92; 514/885,
  514/937, 938, 939, 943

[56] References Cited

U.S. PATENT DOCUMENTS

| | | | |
|---|---|---|---|
| 4,036,953 | 7/1977 | Adam et al. | 424/92 |
| 4,307,229 | 12/1981 | Liav et al. | 536/119 |
| 4,338,334 | 7/1982 | Jensen et al. | 424/322 |
| 4,606,918 | 8/1986 | Allison et al. | 424/88 |

*Primary Examiner*—John F. Terapane
*Assistant Examiner*—Catherine S. K. Scalzo
*Attorney, Agent, or Firm*—Burgess, Ryan & Wayne

[57] ABSTRACT

Vaccines are provided which are composed of (a) non-toxic and highly effective adjuvants obtained from microbial sources, together with (b) tumor antigens. A wide variety of antigens can be employed in the vaccines and include, antigens obtained from tumors or cultures of tumor cells, such as ovarian cancers, melanomas, colorectal cancers, pancreatic cancers, renal cancers and the like. By adding tumor antigens to potent but non-toxic immunostimulants, a protective and lasting tumor immunity can be obtained.

22 Claims, No Drawings

VACCINE CONTAINING TUMOR ANTIGENS AND ADJUVANTS

This application is a continuation-in-part of U.S. application Ser. No. 852,120 now U.S. 4,806,352 filed Apr. 15, 1986 and which is incorporated hereby by reference.

FIELD OF THE INVENTION

This invention relates, in general, to tumor vaccines. In one aspect, this invention is directed to a vaccine composed of non-toxic and highly effective adjuvants from microbial sources and tumor associated antigens. In a further aspect, this invention is directed to a process for the preparation of tumor vaccines and to a method for their use in the treatment and prevention of tumors by enhancing the efficiency of immunogenic tumor antigens.

BACKGROUND OF THE INVENTION

Endotoxin has been recognized over the last ninety years as a potent immunoactivator. W. B. Coley reported in *Ann. Surg.* 14 199 (1891) the use of "Bacterial Toxins" in cancer treatment. It was also reported in *JAMA* 54 250 (1919) that the cure rate in inoperable patients utilizing such a mixed microbial vaccine was 4-7 percent. Endotoxin extracts were subsequently studied in several animal models. Gratia and Linz in *Comp. Rend. Soc. De Biol.* 108: 427 (1931) described hemorrhagic necrosis and concomitant tumor regression in a transplantable liposarcoma model in guinea pigs. Other rodent tumor models followed: sarcoma 180 in mice (Shwartzman, G. and Michailovsky, N., *Proc. Soc. Exp. Biol. Med.* 29: 737 (1932)), Ehrlich carcinomas in mice (Berendt, M. J. and North, R. J., Exp. Med., 151: 69 (1980)), and transplantable tumors in rats (Berendt, M. J. and North, R. J., private communication.).

Recent work on the observation of tumor necrosis in endotoxin-treated animals indicates that the endotoxic fraction itself may not be directly responsible for necrosis (Carswell, E. A., Old, L. J., Kassel, R. L., Green, S., Liore, N., and Williamson, B., *Proc. Nat'l Acad. Sci. USA* 72: 3666 (1975)). Instead, necrosis formation may be mediated by a factor termed tumor necrosis factor (TNF) which has been isolated from mice previously stimulated by macrophage activators such as BCG, *C. parvum* or zymosan. In addition, TNF has been shown to be cytotoxic against certain tumor lines in vitro, and antitumor activity has been ascribed to this substance in vivo.

Prior to the present invention and during a search for microbial components having antitumor activity, it was found that when certain preparations of endotoxin were combined with trehalose dimycolate (TDM) and oil droplets and injected into established malignant line-10 tumors in Strain 2 guinea pigs, a high rate of cures and systemic tumor immunity developed. This led to a reinvestigation of the value of endotoxin as an immunotherapeutic agent. The most powerful endotoxin adjuvants were phenol-water (PQ) or chloroform methanol (CM) extracts from Re (heptoseless) mutant, gram-negative bacteria. These extracts contained endotoxic lipopolysaccharides (LPS) which made up phenol-water extracts from wild-type bacteria. Both ReG1 and lipipolysaccharide when injected in combination with TDM and oil droplets caused a rapid developing Shwartzman-like necrotic reaction in the tumors. Following this reaction, the LPS combination led to only a partial regression of injected tumors, and their growth continued after about two weeks. In contrast, injection of the ReG1-TDM combination led to high rates of permanent regression and development of systemic immunity against a challenge with line-10 tumors. Tumor regression with ReG1+TDM or CWS+TDM and more advanced tumors could be treated with greater success.

In a paper by Dr. J. L. Cantrell et al appearing in *Cancer Research* 39, 1159–1167, April (1979) it was disclosed that a combination of chemotherapy and immunotherapy are highly effective in causing regression of an established tumor in mice, whereas either treatment alone was ineffective. In this study, the immunotherapy used involved injection of KCl - extracted tumor antigens in oil-in-water emulsions with or without trehalose dimycolate.

Also in U.S. Pat. Nos. 4,436,727 and 4,505,903 various combinations of refined detoxified endotoxin or purified pyridine soluble extracts of microorganisms with cell wall skeleton and/or trehalose dimycolate were disclosed as being useful in the treatment of cancerous tumors. However, prior to the present invention, immunotherapy was performed with biological response modifiers, as non-specific immunotherapy or with tumor antigens alone. However, non-specific immunotherapy had only a short effect on tumors and tumor antigens were low in immunogenicity. In addition, the adjuvants previously available for use in human vaccine had low activity, and hence the immunotherapy was not entirely satisfactory. Thus, while there is considerable prior art on adjuvants and on tumor antigens, there is no prior art on the use of non-toxic biological adjuvants to enhance protective immunity when used in combination with tumor antigens. Therefore, what was needed was a potent but non-toxic immunostimulant which could be utilized in conjunction with tumor associated antigens to provide a protective and lasting tumor immunity.

Accordingly, one or more of the following objects will be achieved by the practice of this invention. It is an object of this invention to provide a vaccine which is effective in thie treatment and prevention of tumors. Another object of this invention is to provide a vaccine comprised of non-toxic and highly effective adjuvants from microbial sources and tumor antigens. A further object of this invention is to provide a method for enhancing the antitumor activity of immunogenic tumor antigens. Another object of this invention is to provide a process for the preparation of tumor vaccines. A still further object is to provide a process for the preparation of tumor vaccines comprised of adjuvants and tumor antigens. Another object is to provide a process for the preparation of vaccines comprised of refined, detoxified endotoxins and tumor antigens. A further object is to provide a method for using the vaccines in the treatment and prevention of tumors. These and other objects will be readily apparent to those skilled in the art in light of the teachings contained herein.

SUMMARY OF THE INVENTION

As hereinbefore indicated, the present invention is directed to vaccines comprised of non-toxic and highly active adjuvants obtained from microbial sources and tumor antigens. The invention also relates to processes for preparation of the vaccines and their use in the treatment and prevention of tumors.

The vaccines of the present invention are comprised of:
(a) at least one tumor associated antigen, Monophosphoryl lipid A obtained from lipopolysaccharides of *Salmonella minnesota* R595 has been given as follows:

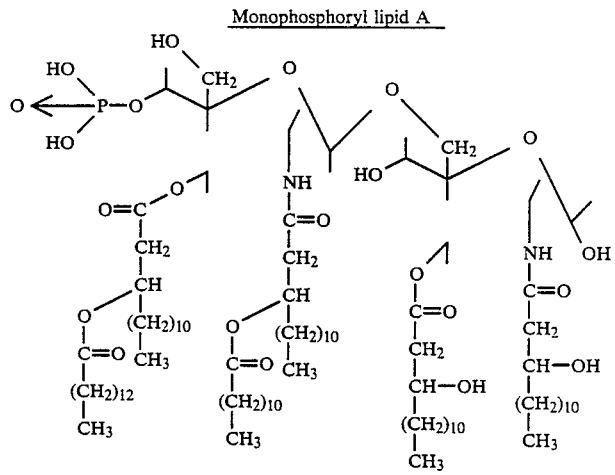

Monophosphoryl lipid A (b) a refined detoxified endotoxin immunostimulant
(c) at least one additional immunostimulant selected from the group consisting of:
  (1) microbacterial cell wall skeleton
  (2) trehalose dimycolate, and
  (3) a pyridine soluble extract of a microorganism, and
(d) a pharmaceutically acceptable carrier.

DETAILED DISCUSSION OF THE INVENTION

As indicated, the vaccines of the present invention are comprised of a tumor associated antigen hereinafter also referred to as (TAA), a refined detoxified endotoxin immunostimulant referred to as (MPL) and at least one other bacterial immunostimulant. The tumor associated antigens which are employed in the vaccines of the present invention can be whole cells, fraction of cells or extracts of tumor cells prepared by known techniques. In some instances it might be desirable to utilize two or more antigens in the same vaccine.

Illustrative tumor associated antigens include but are not limited to antigens obtained from warm-blooded animal tumors such as ocular carcinoma, sarcoid, ovarian cancer, mammary tumors, adenocarcinoma, pancreatic carcinoma, renal carcinoma, lung carcinoma and the like.

The refined detoxified endotoxin immunostimulant employed in the present invention is identified as monophosphoryl lipid A (MPL), and is prepared in the manner set forth in U.S. Pat. Nos. 4,436,727 and 4,436,728 which are incorporated herein by reference. Endotoxin extracts of the type used as the starting material to produce MPL may be obtained from any Enterobacteriaciae including parent organisms and mutants. The aforesaid patents describe the type of microorganisms that may be used to obtain the starting material and several methods for preparing the starting material. The detoxified endotoxin can also be prepared synthetically and by genetic engineering techniques. The preferred method to date of obtaining the endotoxic extract is that disclosed by Chen et al., J. infect. Dis. 128 543 (1973).

Monophosphoryl Lipid A (MPL), is a composition characterized as having no detectable 2-keto-3-deoxyoctonoate, between about 350 and 475 nmoles/mg of phosphorus and between about 1700 and 2000 nmoles/mg of fatty acids. The complete structure of a MPL is a significant improvement over endotoxic extracts obtained from Enterobacteriaciae because MPL is detoxified and therefore does not contain the highly toxic components which have rendered endotoxic extracts unsuitable for therapeutic use. (See *Peptides as Requirements for Immunotherapy of the Guinea-Pig Line-10 Tumor with Endotoxins;* Ribi, et al. Cancer Immunol. Immunother. Vo. 7, pp 43–58: 1979, incorporated herein by reference. The beneficial effects of MPL over other endotoxic extracts is described for example in U. S. Patents Nos. 4,436,727 and 4,436,728; and Ribi, E. Journal of Biological Response Modifiers, Vol 3, pp 1–9: 1984, incorporated herein by reference).

As indicated above, the endotoxin immunostimulant employed in the vaccines of the invention has been detoxified in accordance with the procedures set forth in U. S. Patents 4,436,727 and 4,436,728. By "detoxified" is meant that the toxicity ($LD_{50}$ value) of the endotoxin, based on chick embryo lethality assay, is more than 20 micrograms when compared to the toxic endotoxin where the $LD_{50}$ value is approximately 0.001 micrograms.

In addition to the monophosphoryl lipid A immunostimulant employed in the vaccine of the invention, at least one additional bacterial adjuvant is also present. As indicated above, such adjuvants include (a) mycobacterial cell wall skeleton, (b) trehalose dimycolate and (c) a pyridine soluble extract of a microorganism.

The first bacterial adjuvant which can be employed with the antigen and MPL is the cell wall skeleton which is essentially cell wall which has had much of the protein and lipids normally found in the cell wall removed. It is a polymeric mycolic acid arabinogalactan mucopeptide containing remnants of trehalose mycolates ("P3") and undigested tuberculoproteins. Cell wall skeleton is obtained from any microorganism including, but not limited to, *M.smegmatis, M.phlei, Nocardia rubra, Nocardia asteroides, Corynebacterium diphtheria, Corynebacterium parvum, M.kansaii. M.tuberculosis* (Strain H 37 and RV and Ayoma B), and *M.bovis* Strain BCG. Additionally, cell wall skeleton may be obtained from such other organisms as *E.coli, B.abortus* and *Coxiella burnettii.*

Cell wall skeleton may be produced by first growing and harvesting bacteria such as *M.bovis* strain BCG (Bacillus Calmette-Guerin). The resulting whole cell residue is processed through a cell fractionator [Ribi Cell Fractionator (Sorvall. Model RF-1)] which disrupts the cells, separating the outer envelope or cell wall from the protoplasmic impurities. The resulting cell walls are then subjected to a series of solvent extractions and enzymatic treatments (e.g. trypsin and/or chymotrypsin) to give purified cell wall skeleton.

A second bacterial adjuvant which can be utilized in the vaccines of this invention are the trehalose dimycolates (TDM) which may be obtained from organisms such as, for example, *M.avium. M.phlei, M.tuberculosis* (strain H 37 RV and Ayoma B), *M.bovix* BCG, *M.smegmatis, M.kansaii, Nocardia rubra, M.bovinis* and *Corynebacterium diphtheriae.*

Bacteria such as *M.avium* are grown, harvested and then heat killed. The cell mass is then extracted with several solvents and then an active solvent soluble, fraction is extracted. This extract is further purified by a series of solvent extractions to provide crude TDM (see *Biologically Active Components from Mycobacterial Cell Walls.* 1. *Isolation and Composition of Cell Wall Skeleton and Component,* P. 3; Azuma et al., Journal of the National Cancer Institute, Volume 52, pgs. 95–101, 1974) incorporated herein by reference. As disclosed in Azuma et al., crude TDM may then be further purified by centrifugal microparticulate silica gel chromatography to give purified TDM. TDM may also be prepared as disclosed in U. S. Patent 4,505,900 which issued March 19, 1985.

The third bacterial adjuvant which can be included in the vaccines of the present invention is a pyridine-soluble extract of a microorganism containing between about 3 and 20% by weight of protein, between about 10 and 40% by weight of sugar and about 35 to 60% by weight of fatty acids. The extract preferably contains about 5% by weight of each protein, about 35% by weight of sugar and about 5% by weight of fatty acids.

The protein comprises amino acids and ammonia and the amino acids include, for example, the following:

| | |
|---|---|
| Asparginine | 0.273 |
| Threonine | 0.108 |
| Serine | 0.585 |
| Muramic acid | 0.219 |
| Glutamic acid | 0.267 |
| Glycine | 0.39 |
| Alanine | 0.173 |

The amounts expressed above are in terms of weight percent and the total protein is 6.34% by weight.

The pyridine soluble extract prepared in accordance with the teachings of this invention has been found to have the following elemental analysis:

| Element | Weight Percent |
|---|---|
| Carbon | 60.35 |
| Hydrogen | 9.47 |
| Oxygen | 23.91 |

Additionally the extract is characterized by an infrared spectrum wherein the important peaks useful in identifying the extract are set forth in Table 1 below:

| Peak Frequency* ($cm^{-1}$) | Identification |
|---|---|
| 3400(b) | NH Stretch |
| 3200–2500(b) | Intramolecular hydrogen bonded OH peak |
| 2920(s) | CH Stretch |
| 1710(s) | Ester carbonyl Stretch |
| 1675(s) | Amide carbonyl Stretch (Amide I Band) |
| 1541(m) | Amide II Band |

*(b) = broad
(s) = strong
(m) = moderate

Any microorganism may be used to obtain the pyridine-soluble extract including, for example, M.bovis BCG, *M.phlei, M.smegmatis, M.kansaii, Nocardia rubra, Corynebacterium diphtheriae* and *Corynebacterium parvum. Corynebacterium parvum* is especially preferred.

Whole cells of the microorganism, preferably in the form of a paste, are mixed with pyridine. The resulting mixture is separated to obtain a supernatant fraction which contains the pyridine-soluble extract and a pyridine residue. Optionally, the pyridine residue may be subjected to repeated separation procedures as described above using pyridine to remove further quantities of the desired extract.

The pyridine is then removed from the extract and the dried extract is dialyzed against a suitable liquid such as distilled water. The absence of whole cell and cell fragment contaminants is confirmed by electron microscopy. The resulting purified extract may then be lyophilized by known methods to obtain a stable project.

The immunological adjuvants of the present invention in admixture with the tumor associated antigens enhance the immune response against such antigens and hence are useful in a variety of vaccines tumors in for both animal and human hosts. In practice it has been found that the refined detoxified endotoxin (MPL) is used in a concentration of from about 10 to about 500 micrograms per dose with a particularly enhanced immune response being elicited at concentration of from about 10 to about 50 micrograms per dose. The cell wall skeleton is preferably used in concentration of from about 275 to about 325 micrograms per dose. The trehalose dimycolates are preferably used in a concentration of from about 50 to about 300 micrograms per dose, and more preferably from about 125 to about 175 micrograms per dose. The pyridine-soluble extract can be used in a concentration of from about 500 to about 2400 micrograms per dose and more preferably from about 750 to about 1200 micrograms per dose. If desired, other components or additives can be employed in conjunction with the adjuvants of the present inventions.

In those instances wherein only one or two of the three classes of adjuvants are employed with the antigen and MPL, the concentrations of such adjuvants may be adjusted to higher levels. All that is needed, however, is an immune response enhnacing amount of the adjuvant(s) which will enhance the immune response of the vaccine against the tumor associated antigen(s).

The optimum amount of antigen employed in the vaccines of the present invention will, of course, vary for each particular tumor. In practice, however, it has been found that the antigen is generally present in the vaccine in a concentration of from about 1 to about 100 mg per dose, and more preferably, from about 2 to about 10 mg per dose.

The tumor associated antigens and the adjuvants are preferably employed in a pharmaceutically acceptable carrier to form the vaccine of this invention. Illustrative carriers which can be employed include, physiological saline or oil droplet emulsions. The amount of oil used is in the range of between about 0.5 and about 3.0 pecent by volume based on the total volume of the composition.

Preparation of the vaccines of this invention can be accomplished by blending the TAA, MPL and biological adjuvants in accordance with accepted techniques.

As described above the composition for treatment of warm blooded animals and humans may be used in the form of an oil droplet emulsion. The amount of oil used is in the range of between about 0.5 and 3.0 percent by volume based on the total volume of the composition. It is preferred to use between about 0.75 and 1.5 percent by volume of the oil. Examples of such oils include light mineral oil, squalane, 7-n-hexyloctadecane. Conoco superoil and Drakeol 6 VR mineral oil (produced by the Pennreco Company, Butler, Pa.).

The homogenized oil containing mixture is then combined with a detergent which may optionally be dissolved in a saline solution prior to mixing. The amount of detergent is typically between about 0.02 and 0.20 percent by volume and preferably between about 0.10 and 0.20 percent by volume based on the total volume of the composition. Any common detergent material may be used including Tween-80, and Arlacel (produced by the Atlas Chemical Company).

The mixture resulting from the addition of detergent is then homogenized to form a suspension which has a high percentage of oil droplets coated with MPL and CWS as determined by observation under a microscope.

Alternatively, aqueous suspensions of TAA may be added to lyophilized emulsions containing the biological adjuvants and mixed or emulsified by vortexing until a slight milky suspension is obtained. Lyophilized emulsions are prepared as previously described (See U.S. Patent No. 4,520,019).

The vaccines of the present invention are usually administered to a warm blooded animal by intramuscular, intraperitoneal or subcutaneous injections once a week for up to a total of 15 injections in the doses indicated above.

It has been found that the vaccines of the present invention greatly enhance the immune response against a wide variety of natural tumor associated antigens; and both natural and synthetic viral, bacterial, fungal, or protozoan antigens. The only requirement of the antigen which is employed in the vaccines of the present invention is that it be capable of eliciting an immune response in a host and that the response will be enhanced by the adjuvants of this invention with which it is combined. Thus, the vaccines of the present invention have a potent anti-tumor activity and accordingly are useful in the treatment and prevention of a variety of tumors in both animals and humans. Tumors, including cancers, which may be treated by the vaccines include animal tumors such as bovine squamous cell carcinoma, bovine fibrosarcoma, equine sarcoid, equine melanoma, equine squamous cell carcinoma, canine mammary tumors, canine adenoma and canine melanoma, and human tumors such as ovarian cancers, melanomas, colorectal cancers, pancreatic cancers, renal cancer, and the like.

While not wishing to be bound by the mechanism as to how the vaccines of the present invention bring about tumor regression, it is believed that the combination of the tumor associated antigens and the adjuvant stimulate both a non-specific and specific immune response.

Although the vaccines of the present invention are effective in the treatment of tumors, in practice, these anti-tumor vaccines can be used in a clinical setting as a companion treatment to other forms of therapy. This is because immunotherapy can be most effective when the tumor burden is small enough that it can be handled by the patient's immune system. Thus, a patient with advanced disease would probably undergo some form of treatment to reduce the tumor burden, and subsequently would receive the anti-tumor vaccine in order to eliminate the residual tumor cells. The companion treatment may be surgery, chemotherapy, or radiation therapy, or any other method of effectively reducing the tumor burden. The companion treatment may even entail another form of immunotherapy, such as, for example, administration of interleukin-2.

In the examples which follow, the bacterial components, tumors and tumor cells, and tumor cell vaccines were prepared and evaluated employing procedures known in the art.

EXAMPLE 1

Preparation of Bacterial Components

1. Preparation of Detoxified endotoxin or monophosphoryl lipid A (MPL)

Crude endotoxin is isolated from the polysaccharide-deficient heptoseless Re mutant of *Salmonella minnesota* (strain R595) by organic solvent extraction. This strain was obtained from NIH, NIAID, Rocky Mountain Laboratory, Hamilton, Montana. This endotoxin, which consists only of KDO and lipid A, is a glycolipid rather than a typical endotoxic lipopolysaccharide and is purified by fractional precipitation with organic solvents of appropriate polarities. It is then treated with boiling 0.1 N hydrochloric acid to yield a complex mixture consisting of free fatty acids and structural homologs of non-toxic monophosphoryl lipid A (MPL). These components are separated by pressure elution column chromatography. Eluted fractions corresponding to structural homologs of MPL, as identified by thin-layer chromatography, are pooled and tested for toxicity. They qualify for experimentation in animals when their 50% lethal dose for intravenously inoculated chicken embryos (CELD$_{50}$) is greater than 10 $\mu$g. (The lethal dose for the parent endotoxin is less than 0.001 $\mu$g.)

2. Preparation of Mycobacterial Cell Wall Skeleton (CWS)

Cell walls of *Mycobacterium bovis*, strain BCG obtained from NIH, NIAID, Rocky Mountain Laboratories, Hamilton, Montana are prepared with the aid of the Sorvall-Ribi Cell Fractionator (Model RF-1). By using a pressure of 35,000 psi at a temperature of 10°-15° C., the mycobacterial cell walls are "cracked", and the protoplasm is extruded in a soluble state. Cell wall envelopes are then harvested by centrifugation and purified by repeated centrifugation and resuspension in water. The cell walls are then treated with RNA-ase and DNA-ase to remove nucleic acids followed by a series of proteolytic enzymes and a detergent treatment to remove proteins and peptides, respectively. Finally the preparation is exhaustively extracted with organic solvents to remove "free lipid". The resulting CWS is composed of a polymeric mycolic acid-arabinogalactanmucopeptide complex.

3. Isolation and Purification of Trehalose-Dimycolate (TDM)

Whole cells of mycobacteria are extracted first with ethanol followed by acetone, and finally with a mixture of chloroform and methanol (CM 2:1). The CM extract contains the TDM plus contaminating lipids having lower or higher polarities than TDM. These lipids are selectively separated by precipitating them with compositions of organic solvents in which they are insoluble while retaining the TDM in a soluble phase. The resulting "crude TDM" is purified by pressure elution chromatography. Eluted fractions containing a single component of TDM as determined by TLC are pooled and used for study.

4. Pyridine Extraction of Corynebacterium Parvum (PE)

Heat-killed whole cells of *C. parvum* VPI 0204 obtained from Dr. C. Cummings, Virginia Polytechnic Institute, are extracted three times with pyridine at 37° C. and the combined pyridine soluble extracts are concentracted by flash evaporation, dialyzed and lyophilized. A substance with enhance anti-tumor activity and greatly reduced toxicity is obtained.

EXAMPLE 2

Preparation of Murine Tumor Models to be Evaluated

1. Animals

All tumor experiments ae performed on 6-8 week old C3HB/FeJ female mice or on C57BL/10 and DBA/2 mice of either sex. Mice are obtained from production colonies of Ribi ImmunoChem Research, Inc., Hamilton, Montana. Parental stocks of DBA/2 and C3HB/FeJ mice are purchased from the Jackson Laboratory (Bar Harbor, Maine).

Sewell-Wright guinea-pigs of inbred strain-2 are obtained from the production colony of Ribi Immuno- Chem Research. Guinea-pigs of either sex will weigh 350–500g on entry in the experiments.

2. Tumors

Leukemia EL-4 (Provided by Dr.Bruce Chesebro NIAID, Rocky Mountain Laboratory, Hamilton, Montana), ovarian MOT (from Dr. J. Berek, UCLA, Los Angeles, Ca.), and lymphoma P388 cells obtained from ATCC are maintained in the ascitic form by serial transfers in C57BL/10, C3HB/FeJ, and DBA/2 mice, respectively. Tumor cells are harvested from the peritoneal cavity and washed with 20 ml phosphate buffered saline (PBS). Red blood cells (RBC) are lysed with 10 ml of 1% ammonium oxalate. After 30 sec., physiological osmolarity is restored by the addition of 40 ml PBS. Cells are pelleted by centrifugation, and the cell dose is adjusted so that an inoculum of 2 to $5 \times 10^4$ cells was administered in 0.1 ml of PBS. Line -10 hepatoma cells are maintained in ascitic form in syngeneic strain 2 guinea-pigs by serial i. p. transfer.

Tumor cells are harvested from ascites-bearing donors, washed three 3 times in sterile saline, and adjusted to $20 \times 10^6$ tumor cells/ml.

3. Design of Immunotherapy Experiment

EL-4, MOT, or P388 tumor cells obtained from the same source as indicated above are prepared as described above and 0.2 ml of tumor cell suspension is inoculated i. p. in the appropriate syngeneic strain of mice on day 0. Tumor controls receive no further treatment. At various times (day 1 to day 6) after tumor transplantation, mice are given a single i. p. injection of the immunotherapeutic. Animals in each group are observed daily to determine percentage survival and/or reduction in tumor mass. The line-10 tumor is established in guinea-pigs by intradermal injection of $10^6$ ascites-grown tumor cells. The immunotherapeutics are administered in 0.4 ml volumes by intralesional inoculation after 6 days, at which time the tumors are 9–11 mm in diameter.

EXAMPLE 3

Formulation Procedures for Preparation of Tumor Cell Vaccines

1. Preparation of Solubilized Tumor Associated Antigen(s)

Tumor antigen is prepared by a modified procedure using 3 M KCl extraction. Briefly, 3 M KCl in PBS is added to a cell pellet of live tumor cells at a concentration of 5 m$\frac{1}{8} \times 10^8$ cells. The suspension is stirred for 18 to 24 hours at 4°, after which the pellets are discarded and the supernatant fluid is dialyzed against distilled water for 24 hours at 4° and then centrifuged at 100,000 x g for 2 hours at 4°. The dialysate is finally centrifuged at 100,000 x g for 2 hours at 4° to remove the fine gelatinous precipitate that forms after dialysis. The soluble material is then lyophilized.

The Line-10 guinea-pig tumor; murine E1–4, MOT, and P388; as well as bovine ocular squamous cell carcinoma (BOSCC) and equine sarcoid (ES) obtained from tumor bearing hosts were extracted extracted in this manner. In addition saline suspensions of homogenized BOSCC and ES are extracted by a modified phenol procedure.

2. Preparation of Oil Droplet Emulsion

Oil droplet emulsions contained soluble extracts of the tumors are parepared with varying combinations of CWS, TDM, and MPL as described previously (U.S. Pat. No. 4,520,019).

3. Preliminary Testing of Tumor Vaccines

The methods of therapy are essentially as described previously. Basically, tumors are established by s. c. injection of mice or guinea-pigs with 2 to $5 \times 10^4$ ascites grown tumor cells. Twenty five or 100 μg quantities of mitomycin C are administered intralesionally 7 days after the implantation, when the tumors are about 4 mm in diameter. Two days later, the vaccines are injected by various routes. Cure rates are compared with the survival of untreated animals. Cured animals are tested for capacity to resist a subsequent challenge with homologous tumor cells.

4. Specific Immunotherapy of Spontaneous Tumors of Cattle and Horses

Bovine ocular squamous cell carcinoma (BOSCC) is a potentially metastatic autochthonous carcinoma occurring naturally in about 4.7% of Hereford cattle and in 0.8% - 1.6% of the general cattle population. Equine sarcoid (ES) is a locally aggressive skin tumor and is the most common spontaneous tumor of horses. These tumors do not metastasize readily, but are locally invasive and are nonaggressive.

EXAMPLE 4

Isolation of Tumor Associated Antigens

Two experimental tumor models, (a) line-10 hepatocellular carcinoma in inbred strain 2 guinea-pigs and (b) Murine ovarian tumor (MOT) in inbred C3HB/FeJ mice were obtained from existing breeding colonies of these recipient animals at Ribi ImmunoChem Research, Inc., Hamilton, Montana.

Three following additional murine tumor of cell lines were obtained: L-1210 leukemia was obtained from Dr. Jerry Killion, Oral Roberts University, Tulsa, OK; EL-4 lymphoma tumor cells were obtained from Dr. Bruce Chesebro, NIAID, Rocky Mountain Laboratory, Hamilton, Montana; and P-388 lymphoma tumor cells were purchased from the ATCC. $B_6D_2F_1$ and C3HB/FeJ mice for the maintenance of these tumor cell lines and for tumor regression studies were purchased from The Jackson Laboratory, Bar Harbor, Maine.

Tumor associated antigens (TAA) for use in combination with MPL and other bacterial anti-tumor components of this invention were isolated from MOT ovarian tumor cells, EL-4 lymphoma, P-388 lymphoma and L-1210 leukemia by the 3M KCl extraction method. Briefly, groups of the appropriate strain of mice were given as i. p. injection of 0.5 to $1\times10^5$ viable tumor cells. Ascites fluid was collected 8 to 10 days later and cells removed by centrifugation. Marked tumor cells were extracted overnight with 3M KCl. The aqueous soluble extract was obtained by centrifugation, dialyzed and lyophilized. In addition, TAA was also obtained from ascites grown line-10 tumor cells in strain 2 guinea-pigs using the above procedure.

TAA extracts were also obtained from two spontaneous arising sarcoid tumors in horses. The solid sarcoid tumors were homogenized in 3M KCl and extracted at 4° C. overnight. The aqueous extract was collected by centrifugation, dialyzed and lyophilized.

EXAMPLE 5

Anti-tumor Activity of Detoxified Endotoxin (MPL) Alone or

Combined with Pyridine Extract of *P. acnes* (PA-PE)

Experiments were conducted to show that PA-PE and mycobacteria trehalose dimycolate (TDM) were effective as cell wall skeleton (CWS) in regressing line-10 tumors in strain 2 guinea-pigs when combined with MPL. The results obtained are set forth in Table 1 below:

TABLE 1

Anti-tumor Activity of Oil Emulsions Containing MPL Alone or Combined with PA-PE + TDM in the Line-10 Tumor Model[a]

| Material Injected | Dose | Number Cured Total | % Cured |
|---|---|---|---|
| PE *C. parvum* + MPL + TDM | 500 + 50 + 100 | 17/19 | 89.5 |
| PE *C. parvum* + MPL + TDM | 100 + 50 + 50 | 5/10 | 50 |
| PE *C. parvum* + TDM | 500 + 100 | 3/9 | 33 |
| PE *C. parvum* + MPL | 500 + 50 | 1/9 | 11 |
| PE *C. parvum* only | 500 | 0/7 | 0 |
| MPL + TDM | 500 + 100 | 0/6 | 0 |
| Tumor Controls | — | 0/18 | 0 |

[a]Strain 2 guinea-pigs were inoculated I.D. with $2 \times 10^6$ line-10 tumor cells on day 0. Immunostimulants were administered intralesionally (0.4 ml/animal) on day 6 when the tumors were 8 to 10 mm in diameter.

EXAMPLE 6

The following studies were designed to determine the ability of the aqueous solutions containing MPL alone or in combination with PA-PE to regress MOT ovarian cells in C3HB/FeJ mice. Female mice were inoculated with $2\times10^4$ MOT cells on day 0 and immunotherapy was administered 24 hours later. As shown in Table 2, little or no anti-tumor activity was observed in mice given either 1200 μg of PA-PE or 240 μg or MPL. However, signifigant anti-tumor activity (88% tumor free) was seen in mice treated with the combination of PA-PE +MPL. Moreover, the response was dose dependent in that fewer tumor free animals were seen with decreasing doses of immunostimulants. The results are shown in Table 2 below:

TABLE 2

Anti-tumor Activity of Detoxified Endotoxin (MPL) Alone or Combined with Pyridine Extract of *P. acnes* (PA-PE)[a]

| Material Injected | Dosage (μg) | No. Tumor Free[b] Total No. Injected | Percent Tumor Free |
|---|---|---|---|
| PA-PE + MPL | 1200 + 240 | 43/49 | 88 |
| PA-PE + MPL | 600 + 120 | 4/8 | 50 |
| PA-PE + MPL | 350 + 75 | 0/5 | 0 |
| MPL | 240 | 2/8 | 25 |
| PA-PE | 1200 | 0/8 | 0 |
| None | — | 0/54 | 0 |

[a]Female C3HB/FeJ mice inoculated i.p. with $1-2 \times 10^4$ MOT tumor cells on day 0. Immunostimulants were administered i.p. (0.5 ml/mouse) 24 hours following tumor transplantation.
[b]Number tumor free was determined 60 days after tumor transplantation.

EXAMPLE 7

To determine whether solubilized tumor antigens (TAA) would enhance or add to the antitumor activity of PA-PE +MPL, mice-bearing MOT tumors were given MOT-TAA alone or in combination with a non efficacious dose of PA-PE +MPL (Table 3). No anti-tumor activity was observed in mice treated with 500 or 350 μg of TAA only. However, when 500 μg of TAA was combined with PA-PE +MPL. 1005 of the mice were tumor-free 60 days after tumor transplantation. The mean survival time for the nontreated tumor control group was 21 days. The results are set forth in Table 3 below:

TABLE 3

Efficacy of Tumor Associated Antigens (TAA) Alone or in Combination with PA-PE + MPL in Regressing MOT Tumors in C3HB/FeJ Mice[a]

| Material Injected | Dosage (μg) | No. of Tumor Free[b] Total No. Injected | Percent Tumor Free |
|---|---|---|---|
| TAA | 500 | 0/8 | 0 |
| TAA | 350 | 0/5 | 0 |
| PA-PE +MPL | 350 + 75 | 0/5 | 0 |
| TAA + PA-PE + MPL | 350 + 350 + 75 | 2/5 | 40 |

TABLE 3-continued

Efficacy of Tumor Associated Antigens (TAA) Alone or in Combination with PA-PE + MPL in Regressing MOT Tumors in C3HB/FeJ Mice[a]

| Material Injected | Dosage (μg) | No. of Tumor Free[b] Total No. Injected | Percent Tumor Free |
|---|---|---|---|
| TAA + PA-PE + MPL | 500 + 300 + 60 | 8/8 | 100 |

[a]Female C3HB/FeJ mice were inoculated i.p. with 1-2 × 10⁴ MOT tumor cells on day 0. Immunostimulants were administered i.p. (0.5 ml/mouse) 24 hours following tumor transplantation.
[b]Number tumor free was determined 60 days after tumor transplantation.

EXAMPLE 8

Although significant anti-tumor activity was observed with TAA combined with PA-PE + MPL, it was of interest to determine its anti-tumor effect when administered at increasing times post tumor transplantation. Mice were given 2×10⁴ MOT cells on day 0 and therapy (PA-PE + MPL or TAA + PA-PE + MPL) on day 1,2,3 or 4. Effective therapy with PA-PE + MPL alone or in combination with TAA was observed when given on day 1 or 2 post tumor cell inoculation. However, on days 3 and 4, the amount of anti-tumor activity as measured by tumor free animals was significantly reduced. This decrease in anti-tumor activity is likely due to an increase in tumor burden. Therefore, studies were designed to reduce tumor burden with chemotherapy using mitomycin C. The results are summarized in Table 4 below:

TABLE 4

Anti-tumor Activity of MPL + PA-PE or TAA + MPL + PA-PE Given at Various Times After Tumor Transplantation.[a]

| Material Injected | Time After Tumor (days) | No. Tumor Free[b] Total No. Injected | Percent Tumor Free |
|---|---|---|---|
| Pa-PE + MPL | 1 | 5/6 | 83 |
| (1200 μg + 240 μg) | 2 | 4/6 | 67 |
|  | 3 | 1/6 | 17 |
|  | 4 | 0/6 | 0 |
| TAA + PA-PE + MPL | 1 | 5/6 | 83 |
| (500 + 300 + 60) | 2 | 4/6 | 67 |
|  | 3 | 1/6 | 17 |
|  | 4 | 0/6 | 0 |
| TAA only (500) | 1 | 0/6 | 0 |
| None | — | 0/6 | 0 |

[a]Female C3HB/FeJ mice inoculated i.p. with 1-2 × 10⁴ MOT tumor cells on day 0. Immunostimulants were administered i.p. (0.5 ml/mouse) at 24 hour intervals following tumor transplantation.
[b]Number tumor free was determined 60 days after tumor transplantation.

EXAMPLE 9

To test the effect of combination chemoimmunotherapy, mice were given MOT tumor cells on day 0 and i.p. mitomycin C on days 2 to 6. Immunotherapy was administered 30 to 36 hours after drug administration. The dosage of mitomycin C used was predetermined by treating tumor bearing mice on day 6 with varying dosages of drug i.p.. A dose of 100 μg was selected based on its lack of toxicity and minimal therapeutic effect (20% regression rate).

Table 5 shows the results of a study where tumor bearing mice were treated with mitomycin C on day 6 and immunotherapy 31 hours later. All mice treated with immunotherapy without prior chemotherapy died of progressive tumor growth (data not shown). However, a 50% response rate was observed in the group receiving drug and TAA + PA-PE + MPL at high dose with minimal activity seen at the lower dosage.

TABLE 5

Effect of Chemotherapy Followed by PA-PE + MPL + MOT − TAA on MOT in C3HB/FeJ Mice[a]

| Material Injected; 31 h post Chemotherapy | dose (μg) | No. in Regression total injected Day 34 | Day 63 | % Responding Day 34 | Day 63 |
|---|---|---|---|---|---|
| TAA | 500 | 0/6 |  | 0 | 0 |
| TAA + PA-PE + MPL | 500 + 300 + 60 | 3/6 | 1/6 | 50 | 17 |
| TAA + PA-PE + MPL | 500 + 1200 + 240 | 3/6 | 3/6 | 50 | 50 |
| PA-PE + MPL | 300 + 60 | 0/6 |  | 0 | 0 |
| PA-PE + MPL | 1200 + 240 | 2/6 | 1/6 | 33 | 17 |
| MOT cells only, d0 | — | 0/6 |  | 0 | 0 |

[a]Female C3HB/FeJ mice were inoculated i.p. with 1-2 × 10⁴ MOT tumor cells on day 0. Chemotherapy was given i.p. on day 6 followed by immunotherapy 31 hours later.

EXAMPLE 10

The procedure of Example 9 was repeated with the exception that the time between tumor transplantation and chemotherapy was varied. Immunotherapy was given 33 hours after the drug mitomycin. The results are shown in Table 6 below:

TABLE 6

Effect of Chemotherapy on Days 2,4, or 6 Followed by PA-PE + MPL + MOT − TAA, on MOT in C3HB/FeJ Mice[a]

| Group | Material Injected 33 h post chemotherapy | dose (μg) | No responding d54 Total injected | % responding | MST |
|---|---|---|---|---|---|
| A | PA-PE + MPL | 300 + 60 | 4/6 | 67 | >54 |
| B | PA-PE + MPL | 1200 + 240 | 5/6 | 83 | " |
| C | TAA + PA-PE + MPL | 500 + 300 + 60 | 5/6 | 83 | " |
| D | " | 500 + 1200 + 240 | 6/6 | 100 | " |
| E | " | 1000 + 300 + 60 | 4/6 | 67 | " |
| F | " | 1000 + 1200 + 240 | 5/6 | 83 | " |
| G | Control, MOT cells only | — | 4/6 | 67 | " |
| H | PA-PE + MPL | 1200 + 240 | 5/6 | 83 | >54 |
| I | TAA + PA-PE + MPL | 500 + 300 + 60 | 5/6 | 83 | " |
| J | " | 500 + 1200 + 240 | 6/6 | 100 | " |
| K | " | 1000 + 300 + 60 | 4/6 | 67 | " |

TABLE 6-continued

Effect of Chemotherapy on Days 2,4, or 6 Followed by PA-PE + MPL + MOT − TAA, on MOT in C3HB/FeJ Mice[a]

| Group | Material Injected 33 h post chemotherapy | dose (µg) | No responding d54 Total injected | % responding | MST |
|---|---|---|---|---|---|
| L | " | 1000 + 1200 + 240 | 5/6 | 83 | " |
| M | Control, MOT cells only | — | 0/6 | 0 | 28 |
| N | TAA | 1000 | 1/6 | 17 | 35 |
| O | TAA + PA-PE + MPL | 500 + 1200 + 240 | 3/6 | 50 | 37 |
| P | " | 1000 + 300 + 60 | 3/6 | 50 | 43 |
| Q | " | 1000 + 1200 + 240 | 4/6 | 67 | >54 |
| R | Control, MOT cells only | — | 0/6 | 0 | 24 |
| S | Mot cells only (no drug) | — | 0/6 | | 22 |

[a]Groups A–G, mitomycin day 2;
Groups H–M, mitomycin day 4;
Grouos N–R, mitomycin day 6.

When mitomycin C was administered on day 2, no signifigant difference was observed in those groups receiving chemoimmunotherapy or chemotherapy only. Thus, chemotherapy has a dramatic effect when given early. Conversely no chemotherapeutic effect was seen in animals given the drug only on day 4 or 6 but when combined with immunotherapy, a marked anti-tumor effect was observed. This anti-tumor activity was seen in mice given PA-PE +MPL alone or combined with TAA.

EXAMPLE 11

Anti-tumor Activity of TAA in combination with Other Microbial Anti-tumor Components in Regressing line-10 Tumors in Strain 2 Guinea-Pigs Previous studies have shown that the combination of MPL and cell wall skeleton (CWS) has signifigant anti-tumor activity as measured by regression of established line-10 tumors in strain 2 guinea-pigs. The following study was designed to determine whether the addition of solubilized TAA to the MPL +CWS would enhance its anti-tumor activity. Inbred strain 2 guinea-pigs were inoculated with $2 \times 10^6$ viable line-10 tumor cells on day 0. Immunotherapy was given directly into the tumors as oil-in-water emulsions on day 6 when tumors were 8 to 10 mm in diameter. Results are shown on Table 7.

TABLE 7

Anti-tumor Activity of Tumor Associated Antigen in Combination with Various BRM Formulations on Line-10 Hepatocarcinoma in Strain 2 Guinea Pigs

| Material Injected | dose (µg) | No. Tumor Free total injected | % Tumor Free (day 84) |
|---|---|---|---|
| Triple mixture (CWS + MPL + TDM) | 50 + 50 + 50 | 3/7 | 43 |
| L10-TAA + Triple mixture | 1000 50 + 50 + 50 | 5/7 | 71 |
| DETOX (CWS + MPL) | 200 + 20 | 1/7 | 14 |
| Li0-TAA + DETOX | 1000 200 + 20 | 2/7 | 29 |
| L10-TAA only | 1000 | 0/7 | 0 |

[1]Results shown are for intratumor injection. No anti-tumor activity was observed (0/7) when these combination were given in contralateral flank.

Although the invention has been illustrated by the preceding examples, it is not to be construed as being limited to the materials disclosed therein; but rather the invention is directed to the generic area as hereinbefore disclosed. Various modification an embodiments can be made without departing from the spirit or scope thereof.

What is claimed is:

1. A vaccine useful for the treatment and prevention of tumors in a host, said vaccine comprised of:
   (a) at least one tumor-associated antigen,
   (b) a refined detoxified endotoxin immunostimulant, and
   (c) at least one biological immunostimulant selected from the group consisting of:
      (1) mycobacterial cell wall skeleton
      (2) trehalose dimycolate, and
      (3) pyridine soluble extract of a microorganism, and
   (d) a pharmaceutically acceptable carrier.

2. The vaccine of claim 1 wherein said refined detoxified endotoxin has no detectable 2-keto-3-deoxyoctonoate between about 350 and 475 nmoles/mg of phosphorus and between about 1700 and 2000 nmoles/mg of fatty acids.

3. The vaccine of claim 1 wherein said refined detoxified endotoxin is monophosphoryl lipid A.

4. The vaccine of claim 1 wherein component (c) is mycobacterial cell wall skeleton.

5. The vaccine of claim 1 wherein component (c) is trehalose dimycolate.

6. The vaccine of claim 1 wherein component (c) is a pyridine soluble extract of a microorganism.

7. The vaccine of claim 1 wherein component (c) is a combination of mycobacterial cell wall skeleton and trehalose dimycolate.

8. The vaccine of claim 1 wherein component (c) is a combination of mycobacterial cell wall skeleton and a pyridine soluble extract of a microorganism.

9. The vaccine of claim 1 wherein component (c) is a combination of trehalose dimycolate and a pyridine soluble extract of a microorganism.

10. The vaccine of claim 1 wherein component (c) is a combination of mycobacterial cell wall skeleton, trehalose dimycolate and a pyridine soluble extract of a microorganism.

11. The vaccine of claim 1 wherein said pyridine soluble extract from said microorganism contains between about 7 and 20% by weight of protein, between about 10 and 16% by weight of sugar, and between about 35 and 55% by weight of fatty acids.

12. A process for the preparation fo a vaccine useful for the treatment and prevention of tumors in a host which comprises forming a mixture of:
   (a) at least one tumor associated antigen
   (b) a refined detoxified endotoxin
   (c) at least one biological immunostimulant selected from the group consisting of:
      (1) mycobacterial cell wall skeleton
      (2) trehalose dimycolate, and
      (3) pyridine soluble extract of a microorganism, and (d) a pharmaceutically acceptable carrier

13. A process for the treatment and prevention of tumors in a host, which comprises administering to said host an anti-tumor effective amount of a vaccine comprised of:
- (a) at least one tumor associated antigen,
- (b) a refined detoxified endotoxin immunostimulant, and
- (c) at least one biological immunostimulant from the group consisting of:
  - (1) mycobacterial cell wall skeleton,
  - (2) trehalose dimycolate, and
  - (3) pyridine soluble extract of a microorganism, and
- (d) a pharmaceutically acceptable carrier.

14. The process of claim 13 wherein said refined detoxified endotoxin has no detectable 2-keto-3-deoxyoctonoate, between about 350 and 475 nmoles/mg of phosphorus and between about 1700 and 2000 nmoles/mg of fatty acids.

15. The process of claim 13 wherein said refined detoxified endotoxin is monophosphoryl lipid A.

16. The process of claim 13 wherein component (c) is mycobacterial cell wall skeleton.

17. The process of claim 13 wherein component (c) is trehalose dimycolate.

18. The process of claim 13 wherein component (c) is a pyridine soluble extract of a microorganism.

19. The process of claim 13 wherein component (c) is a combination of mycobacterial cell wall skeleton and trehalose dimycolate.

20. The process of claim 13 wherein component (c) is a combination of mycobacterial cell wall skeleton and a pyridine extract of a microorganism.

21. The process of claim 13 wherein component (c) is a combination of trehalose dimycolate and a pyridine soluble extract of a microorganism.

22. The process of claim 13 wherein component (c) is a combination of mycobacterial cell wall skeleton, trehalose dimycolate and a pyridine soluble extract of a microorganism.

* * * * *